United States Patent [19]

Borrelli et al.

[11] Patent Number: 4,568,543

[45] Date of Patent: Feb. 4, 1986

[54] PHARMACEUTICAL COMPOSITION CONTAINING A FIBRINOLYTIC AGENT AND A DIFFUSION FACTOR, USEFUL FOR THE TREATMENT OF MYOCARDIAL INFARCTION

[75] Inventors: Francesco Borrelli; Francesco Antonetti, both of Rome, Italy

[73] Assignee: Istituto Farmacologico Serono S.p.A., Italy

[21] Appl. No.: 669,462

[22] Filed: Nov. 8, 1984

Related U.S. Application Data

[63] Continuation-in-part of Ser. No. 538,196, Oct. 3, 1983, abandoned.

[30] Foreign Application Priority Data

Oct. 8, 1982 [IT] Italy ................ 49241 A/82

[51] Int. Cl.$^4$ ............................................ A61K 37/48
[52] U.S. Cl. ................................................... 424/94
[58] Field of Search ..................................... 424/94

[56] References Cited

PUBLICATIONS

Hiemeyer et al.–Chem. Abst., vol. 70, (1969), p. 105,084d.

Hofmann et al.–Chem. Abst., vol. 93, (1980), p. 107,011b.

Afonskaya et al.–Chem. Abst., vol. 88, (1978), p. 20142t.

Primary Examiner—Sam Rosen
Attorney, Agent, or Firm—Ostrolenk, Faber, Gerb & Soffen

[57] ABSTRACT

The association of a fibrinolytic agent and of a diffusion factor has been shown very useful in the treatment of myocardial infarction. It has been shown that it is very useful to administer urokinase and hyaluronidase in the quantity ratio of at least 8 to 1, the quantity of each compound being expressed in the appropriate international units.

7 Claims, No Drawings

PHARMACEUTICAL COMPOSITION CONTAINING A FIBRINOLYTIC AGENT AND A DIFFUSION FACTOR, USEFUL FOR THE TREATMENT OF MYOCARDIAL INFARCTION

CROSS REFERENCE TO RELATED APPLICATION

This is a continuation-in-part of application Ser. No. 538,196, filed Oct. 3, 1983, now abandoned.

The term "myocardial infarction" describes the irreversible damaging of the cells as well as the necrosis occurring as a consequence of a total or important reduction of the coronary flow feeding some areas of the cardiac muscle; moreover, it may be a consequence of an insufficient increase of the coronary flow with reference to an increased requirement of oxygen, as may happen under some conditions of stress.

In almost all cases of persons suffering an acute and-/or previous myocardial infarction, one finds in a more or less evident size, a restriction of the inside diameter of the coronary artery as a result of coronary arteriosclerosis or of some other causes.

An exhaustive treatment of the factors involved in cases of myocardial infarction, and of the therapeutic means being used today for it's care, it's prevention, and the reduction of the consequent irreversible damage to the cardiac muscle, may be found in a recent review by J. T. Willerson and L. M. Buja entitled "Causes and Course of the Acute Myocardial Infarction" published in *The American Journal of Medicine*, in December 1980, volume 69, pages 902–914. This review article discusses all current knowledge about the treatment and prevention of myocardial infarction, and represents an exhaustive description of the state of the art; it must therefore be considered incorporated as a reference within the instant text. The importance of coronary thrombosis in the genesis of acute myocardial infarction has been and is still subject to discussion. However, supported by the above-mentioned theoretical base, many authors have experimented successfully with a treatment by means of urokinase given as an intravenous infusion in the care of primary acute myocardial infarction. The usefulness of thrombolytical infarction treatment in its acute stage is still a controversial matter (*Lancet*, 4 October 1975, pp 624-626).

It has been shown recently that streptokinase administered through coronary infusion to some patients suffering myocardial infarction has been successful by causing the re-channeling of the obstructed coronary arteries. However, several secondary effects, such as arrhythmia, have been observed after the intracoronaric administration of streptokinase.

Hyaluronidase, one of the first agents indicated to change and to improve the consequences of coronary artery obstruction, does clearly reduce the extent of the experimentally induced necrosis. Such activity by hyaluronidase has been considered the result of three main mechanisms: the improved supply of nutritional substances to the myocardium; the increased washout of harmful metabolic substances, and the increased collateral hematic flow to the area with a reduced flow of blood.

A purpose of the instant invention is to supply a new preparation for the therapeutic use shown to be of particular advantage in the treatment of myocardial infarction.

Other purposes of the instant invention shall become evident from the following description.

The above-mentioned purposes are obtained by means of a composition containing a fibrinolytic agent, such as urokinase, streptokinase, etc. and moreover a diffusion-promoting agent, such as hyaluronidase.

The protective effect of the composition has been evaluated in an experimental myocardial infarction induced in the rat by means of isoproterenol. In this model, the myocardial lesions are the consequence of aggregation of the platelets within the coronary arteries, all caused by the catecholamines.

The physiologic and pathologic variations in the rats during the acute steps of myocardial necrosis and the reinstatement, are similar to those found in patients, for instance, modifications in the serum values of enzymes, lipids, catecholamines, and steroids, and electrocardiographic alterations.

The experments were carried out on Sprague-Dawley rats whose weight was 225 to 260 grams.

Myocardial infarction was induced by subcutaneous administration of two doses of 85 mg/kg in a volume of 1 ml/kg isoproterenol chlorhydrate with a time interval of 24 hours. Thirty minutes after the first injection of isoproterenol, the animals were treated at random according to the following schedule:

Group 1: Physiologic solution (NaCl 0.9%)
Group 2: Hyaluronidase, 1250 I.U./kg
Group 3: Hyaluronidase, 2500 I.U./kg
Group 4: Hyaluronidase, 3750 I.U./kg
Group 5: Urokinase 20,000 I.U./kg
Group 6: Urokinase, 40,000 I.U./kg
Group 7: Urokinase, 60,000 I.U./kg
Group 8: Hyaluronidase 2,500 I.U./kg+ Urokinase 20,000 I.U./kg
Group 9: hyaluronidase 2,500 I.U./kg+ Urokinase 40,000 I.U./kg A tenth group, which did not receive isoproterenol but which was treated with a normal physiological solution (NaCl 0.9%) was used as a control test group.

Treatments were repeated six hours after the first administration of isoproterenol and again immediately after the second injection of isoproterenol.

All treatments were performed by slow intravenous infusion (0.8 ml/hour) into one of the tail veins.

The drugs were carried in a physiological solution (NaCl 0.9%). A solution containing both urokinase and hyaluronidase was injected into Groups 8 and 9. Six hours after the second injection of isoproterenol, two blood samples from the abdominal aorta were taken from each ether-anesthetized animal. One sample, placed in a plastic test tube containing sodium EDTA, was used to determine the plasmatic levels of the following enzymes: cardiac isoenzyme of lactic dehydrogenase (LDH), glutamic oxalacetic transaminase (GOT) and creatine phosphokinase (CPK). The second sample was placed in a plastic test tube containing sodium EDTA and acetylsalicylic acid (250 ug/ml blood) and was used for determination of plasmatic thromboxane $B_2$ ($TXB_2$) by means of radioimmunoassay.

Immediately after sampling, all animals were sacrificed, the hearts quickly removed and rinsed in a physiologic solution and then carefully examined to ascertain the extent of the necrotic areas. This examination was carried out using the 5 point scoring system proposed by G. Rona et al (AMA *Arch Pathol* 67:443–445, 1959).

The results of the different treatments on the plasmatic levels of CPK, GOT, and LDH are summarized in Table 1.

The administration of isoproterenol causes an increase in the values of CPK, GOT and LDH, respectively, to 92.3, 96.1, and 126.9 I.U. per liter in comparison to the corresponding normal waves.

The administration of hyaluronidase, independent of dose, causes a statistically significant reduction of the plasmatic levels of GOT and LDH, which levels were increased by actions of the isoproterenol. Treatment with urokinase at the doses indicated showed a non-statistically significant inhibition of the levels of the three enzymes (see Table 1).

The simultaneous administration of hyaluronidase (2,500 IU/kg) and urokinase (20,000 I.U./kg) inhibits activity of the plasmatic GOT and LDH action, being statistically significant and comparable in degree to that performed by hyaluronidase alone. On the contrary, when hyaluronidase (2,500 I.U./kg) is administered in association with urokinase (40,000 I.U./mg), one obtains a further, statistically significant reduction of the plasmatic enzymes to 46.3% for GOT and 40.2% for LDH.

As to the plasmatic level of CPK, a significant reduction is obtained in a similar way with all the treatments except the combination of hyaluronidase 2,500 I.U./kg with urokinase 40,000 IU/kg. This combination reduces the CPK values by 42.4% in comparison with the value for the infarcted control animals.

Table 2 shows the data for $TXB_2$. The administration of isoproterenol causes an increase in the plasmatic $TXB_2$ levels in the control group in comparison to normal values. Treatment with hyaluronidase alone, urokinase alone, or any combination of both together, brings the $TXB_2$ levels back to normal values.

A reduction of the necrotic areas has been observed in all animals subjected to treatment. In particular, a reduction of 50% in necrotic areas was observed in the animals treated with the combination of hyaluronidase and urokinase (Table 3).

Finally, the survey of mortality as recorded during the experiments indicates a protective action of treatment with the combination of hyaluronidase (2,500 IU/kg) and urokinase (40,000 IU/kg). As a matter of fact, only this treatment causes a sharp reduction of the mortality incidence to only 12.5% in comparison to the control group which had a mortality level of 38.6%. The results of the various treatments on the mortality levels of rats are summarized in Table 4.

The results indicated above show that the intravenous administration of hyaluronidase together with urokinase reduces or causes some improvement in the infarction experimentally induced by isoproterenol. This observation is based principally upon the study of the plasmatic levels of CPK, GOT and LDH, upon the macroscopic evaluation of the extent of the infarction-damaged areas, and upon the mortality rate. In particular, one may see that sharply and surprisingly higher protective effects are obtained by the simultaneous administration of hyaluronidase (2,500 IU/kg) and urokinase (40,000 IU/kg), as is shown by the GOT and LDH levels, and the mortality rate.

It is important to underline that the protective effects provided by this combination are clearly higher than those exercised by its single components, even when these are used at doses much higher than in the combination.

The pharmaceutical production of the composition in accordance with the invention is not particularly difficult. When the substances are easily lyophilizable, as is the case with urokinase and hyaluronidase, that is the preferred form for reasons of stability. Some excipients may be suitably used in the composition as a part thereof, and this addition does not change in a substantial manner the basic idea, consisting of the simultaneous or consecutive administration of a fibrinolytic agent and of a diffusion factor.

Based upon the results shown above, it is clear that the compositions containing urokinase and hyaluronidase and particularly those compositions containing them in a ratio greater than 8:1 (the quantities being expressed in International Units of biologic activity of the relevant substances) are of particular advantage.

Within the scope of the present invention there are not only the pharmaceutical compositions containing both substances in one container, but also some particular forms of presentation supplying them separately and every form of actuation including and practically carrying out the abovementioned basic therapeutic idea.

TABLE 1

Effects of Hyaluronidase (HYAL), Urokinase (UK) and their combination on the CPK, GOT and LDH plasmatic levels in isoproterenol (ISP) - induced myocardial infarction in rats.

| EXPERIMENTAL GROUP | No. of animals | TREATMENTS ISP (mg/kg s.c.) TWICE | TREATMENTS HYAL (IU/kg, I.V.) 3 TIMES | TREATMENTS UK (IU/kg, I.V.) 3 TIMES | PLASMA LEVELS OF CARDIAC ENZYMES (mean = SE) CPK (U/l) | % inhibit. | GOT (U/l) | % inhibit. | LDH (U/l) | % inhibit. |
|---|---|---|---|---|---|---|---|---|---|---|
| 0 Normal controls | 24 | — | — | — | 35.67 ± 2.81 | — | 31.04 ± 1.42 | — | 18.13 ± 1.30 | — |
| 1 Infarcted controls | 27 | 85 | — | — | 92.26 ± 8.04 | — | 96.14 ± 4.67 | — | 126.92 ± 9.27 | — |
| 2 HYAL I | 17 | 85 | 1,250 | — | * 65.93 ± 7.04 | 28.5 | ** 72.13 ± 8.01 | 24.9 | N.S. 98.54 ± 9.12 | 22.4 |
| 3 HYAL II | 18 | 85 | 2,500 | — | * 61.75 ± 6.47 | 33.1 | ** 69.46 ± 6.48 | 27.7 | * 93.75 ± 6.37 | 26.1 |
| 4 HYAL III | 18 | 85 | 3,750 | — | ** 60.24 ± 6.71 | 34.7 | ** 68.92 ± 8.31 | 28.3 | * 94.16 ± 6.29 | 25.8 |
| 5 UK I | 17 | 85 | — | 20,000 | * 61.84 ± 8.13 | 32.9 | N.S. 76.04 ± 12.30 | 20.9 | N.S. 109.17 ± | 13.9 |
| 6 UK II | 17 | 85 | 13 | 40,000 | ** 60.27 ± 6.56 | 34.6 | N.S. 74.54 ± 11.15 | 22.4 | N.S. 101.24 ± 9.13 | 20.2 |
| 7 UK III | 16 | 85 | — | 60,000 | ** 59.91 ± 7.03 | 35.0 | * 74.68 ± 10.92 | 22.3 | N.S. 99.75 ± 10.02 | 21.4 |
| 8 HYAL II + | 19 | 85 | 2,500 | 20,000 | * 62.56 ± 6.09 | 31.1 | ** 65.75 ± 8.80 | 31.6 | ** 92.57 ± 6.31 | 27.0 |

TABLE 1-continued

Effects of Hyaluronidase (HYAL), Urokinase (UK) and their combination on the CPK, GOT and LDH plasmatic levels in isoproterenol (ISP) - induced myocardial infarction in rats.

| EXPERI-MENTAL GROUP | No. of ani-mals | TREATMENTS ISP (mg/kg s.c.) TWICE | HYAL (IU/kg, I.V.) 3 TIMES | UK (IU/kg, I.V.) 3 TIMES | PLASMA LEVELS OF CARDIAC ENZYMES (mean ± SE) CPK (U/l) | % inhi-bit. | GOT (U/l) | % inhi-bit. | LDH (U/l) | % inhi-bit. |
|---|---|---|---|---|---|---|---|---|---|---|
| 9 HYAL II + UK II | 21 | 85 | 2,500 | 40,000 | *** 53.13 ± 4.20 | 42.4 | *** 51.59 ± 4.15 | 46.3 | *** 75.86 ± 5.94 | 40.2 |

*p < 0.05
**p < 0.01
***p < 0.001
Student's "t" test (calculated vs. infarcted controls).

TABLE 2

Effects of Hyaluronidase (HYAL), Urokinase (UK) and their combined dosages on the plasmatic $TXB_2$ elevation in rats with myocardial infarction induced by isoproterenol.

| Experimental Group | No of animals | TREATMENTS ISP (mg/kg, s.c.) Twice | HYAL (IU/kg, i.v.) 3 times | UK (IU/kg, i.v.) 3 times | PLASMATIC LEVELS OF $TXB_2$ $\bar{x}$ + ES | % variation |
|---|---|---|---|---|---|---|
| 10 Normal controls | 24 | — | — | — | 424.31 ± 41.15 | — |
| 1 Infarcted controls | 27 | 85 | — | — | 636.04 ± 86.75 | +49.90 |
| 2 HYAL I | 17 | 85 | 1,250 | — | 487.83 ± 39.77 | +14.97 |
| 3 HYAL II | 18 | 85 | 2,500 | — | 478.12 ± 47.41 | +12.68 |
| 4 HYAL III | 18 | 85 | 3,750 | — | 475.36 ± 37.35 | +12.03 |
| 5 UK I | 17 | 85 | — | 20,000 | 461.23 ± 46.68 | +8.70 |
| 6 UK II | 17 | 85 | — | 40,000 | 455.78 ± 51.47 | +7.42 |
| 7 UK III | 16 | 85 | — | 60,000 | 463.15 ± 56.17 | +9.15 |
| 8 HYAL II + UK I | 19 | 85 | 2,500 | 20,000 | 447.86 ± 29.91 | +5.55 |
| 9 HYAL II + UK II | 21 | 85 | 2,500 | 40,000 | 437.35 ± 21.82 | +3.07 |

TABLE 3

Effects of Hyaluronidase (HYAL), Urokinase (UK) and their combined dosages on the extent of the myocardial injured areas induced by isoproterenol in rats.

| EXPERIMENTAL GROUP | No. of animals | TREATMENTS ISP (mg/kg, s.c.) TWICE | HYAL (I.U./kg, i.v.) 3 times | UK (I.U./kg, i.v.) 3 times | EXTENT OF MYOCARDIAL INJURED AREAS* 0 | 1 | 2 | 3 | 4 | mean score |
|---|---|---|---|---|---|---|---|---|---|---|
| 1 Infarcted controls | 27 | 85 | — | — | 0 | 0 | 1 | 14 | 12 | 3.40 |
| 2 HYAL I | 17 | 85 | 1,250 | — | 0 | 5 | 0 | 10 | 2 | 2.52 |
| 3 HYAL II | 18 | 85 | 2,500 | — | 1 | 4 | 1 | 11 | 1 | 2.38 |
| 4 HYAL III | 18 | 85 | 3,750 | — | 1 | 4 | 2 | 8 | 3 | 2.44 |
| 5 UK I | 17 | 85 | — | 20,000 | 1 | 3 | 2 | 9 | 2 | 2.47 |
| 6 UK II | 17 | 85 | — | 40,000 | 2 | 2 | 1 | 11 | 1 | 2.41 |
| 7 UK III | 16 | 85 | — | 60,000 | 3 | 1 | 1 | 9 | 2 | 2.38 |
| 8 HYAL II + UK I | 19 | 85 | 2,500 | 20,000 | 5 | 5 | 2 | 7 | 0 | 1.57 |
| 9 HYAL II + UK II | 21 | 85 | 2,500 | 40,000 | 7 | 5 | 2 | 7 | 0 | 1.42 |

*Reported as no of animals assigned to each class of the five point-scoring system.

TABLE 4

Effects of Hyaluronidase (HYAL), Urokinase (UK) and their combined dosages on the mortality rate induced by the injection of isoproterenol (ISP) in rats.

| EXPERIMENTAL GROUP | TREATMENTS ISP (mg/kg, s.c.) TWICE | HYAL (IU/kg, i.v.) 3 times | UK (IU/kg, i.v.) 3 times | MORTALITY RATE No. Survivors/ total No. | Percentge Mortality |
|---|---|---|---|---|---|
| 10 Normal controls | — | — | — | 24/24 | 0 |
| 1 Infarcted controls | 85 | — | — | 27/44 | 38.6 |
| 2 HYAL I | 85 | 1,250 | — | 17/24 | 29.1 |
| 3 HYAL II | 85 | 2,500 | — | 18/24 | 25.0 |
| 4 HYAL III | 85 | 3,750 | — | 18/24 | 25.0 |

TABLE 4-continued

Effects of Hyaluronidase (HYAL), Urokinase (UK) and their combined dosages on the mortality rate induced by the injection of isoproterenol (ISP) in rats.

| EXPERIMENTAL GROUP | TREATMENTS | | | MORTALITY RATE | |
|---|---|---|---|---|---|
| | ISP (mg/kg, s.c.) TWICE | HYAL (IU/kg, i.v.) 3 times | UK (IU/kg, i.v.) 3 times | No. Survivors/ total No. | Percentge Mortality |
| 5 UK I | 85 | — | 20,000 | 17/24 | 29.1 |
| 6 UK II | 85 | — | 40,000 | 17/24 | 29.1 |
| 7 UK III | 85 | — | 60,000 | 16/24 | 33.3 |
| 8 HYAL II + UK I | 85 | 2,500 | 20,000 | 19/24 | 20.8 |
| 9 HYAL II + UK II | 85 | 2,500 | 40,000 | 21/24 | 12.5 |

We claim:

1. A pharmaceutical composition for the treatment of myocardial infarction containing therapeutically effective quantities of urokinase and hyaluronidase in which the urokinase and hyaluronidase are present in a ratio, expressed in international units, of at least 8:1.

2. The pharmaceutical composition of claim 1, wherein said ratio is 16:1.

3. The pharmaceutical composition of claim 1 containing 40,000 International Units of urokinase and 2,500 International Units of hyaluronidase.

4. The pharmaceutical composition of claim 1 in a lyophilized form in ampoules for intravenous use.

5. A method of treating myocardial infarction which comprises administering a therapeutically effective quantity of the composition of claim 1.

6. A method of treating myocardial infarction which comprises administering a therapeutically effective quantity of the composition of claim 3.

7. A method of treating myocardial infarction which comprises administering a therapeutically effective quantity of the composition of claim 4.

* * * * *